United States Patent [19]
Sakamoto et al.

[11] Patent Number: 5,821,388
[45] Date of Patent: Oct. 13, 1998

[54] PROCESS FOR PREPARING α-HALOACETOPHENONE DERIVATIVE

[75] Inventors: Junichi Sakamoto; Hideaki Nishiguchi; Hiroshi Goda, all of Hyogo-ken, Japan

[73] Assignee: Sumitomo Seika Chemical Co., Ltd., Hyogo-ken, Japan

[21] Appl. No.: 834,544

[22] Filed: Mar. 27, 1997

[30] Foreign Application Priority Data

Mar. 28, 1996 [JP] Japan ........................ 8-74575

[51] Int. Cl.$^6$ ................................ C07C 315/02
[52] U.S. Cl. ................................ 568/31; 568/43
[58] Field of Search ...................... 568/43, 31

[56] References Cited

U.S. PATENT DOCUMENTS

| | | | |
|---|---|---|---|
| 2,763,692 | 9/1956 | Gregory | 568/43 |
| 3,150,187 | 9/1964 | Cavsllini et al. | 568/43 |
| 4,490,534 | 12/1984 | Harrid | 546/294 |
| 5,326,862 | 7/1994 | Radisson | 540/456 |

FOREIGN PATENT DOCUMENTS

| | | | |
|---|---|---|---|
| 2537132 | 12/1982 | France | 568/31 |
| 94/15932 | 7/1994 | WIPO | 568/31 |

OTHER PUBLICATIONS 1-(4-Alkanesulfonylphenacyl)-4-Arylpiperazines and Related Compounds; A New Series of Central Depressants, Z.J. Vejdelek, et al., Collection Czechoslov. Chem. Commun. [vol. 40] 1975, pp. 1204–1217.

*Primary Examiner*—James H. Reamer
*Attorney, Agent, or Firm*—Knobbe, Martens, Olson & Bear, LLP

[57] ABSTRACT

The present invention provides processes for preparing α-halo(methylthio)acetophenone and α-halo(methylsulfonyl)acetophenone in an industrially simple and economically advantageous manner. In the invention, methylthioacetophenone is halogenated with a halogenating agent in the presence of an alcohol, giving α-halo(methylthio) acetophenone. Then the compound is oxidized with an oxidizing agent, giving α-halo(methylsulfonyl) acetophenone.

15 Claims, No Drawings

PROCESS FOR PREPARING α-HALOACETOPHENONE DERIVATIVE

FIELD OF THE INVENTION

The present invention relates to novel processes for preparing α-halo(methylthio)acetophenone and α-halo(methylsulfonyl)acetophenone from methylthioacetophenone. α-Halo(methylthio)acetophenone and α-halo(methylsulfonyl)acetophenone are useful compounds, for example, as an intermediate for preparing pharmaceuticals.

BACKGROUND OF THE INVENTION

There have been known processes for preparing α-halo(methylthio)acetophenone and α-halo(methylsulfonyl)acetophenone as below: (1) Collect. Czech. Chem. Commun., 40, 1204 (1975)

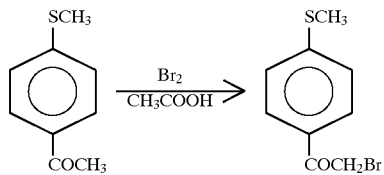

(2) WO 94/15932

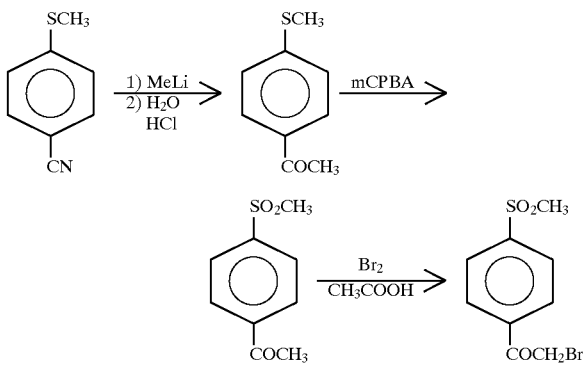

(3) FR 2537132

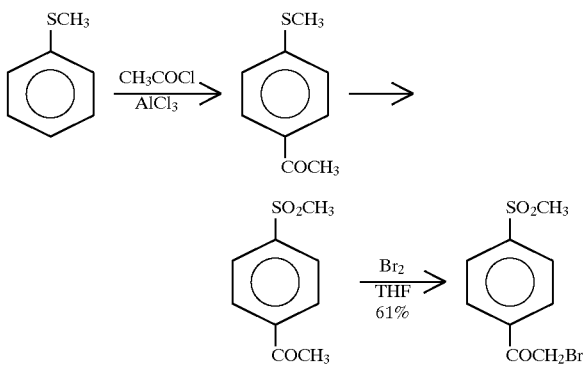

In a process for preparing α-bromo(methylthio)acetophenone, bromination is generally carried out in an acetic acid solvent as illustrated in (1). The process produces a mixture of the desired α-bromo(methylthio)acetophenone, unreacted methylthioacetophenone and, as a by-product, α-dibromo(methylthio)acetophenone. Hence, the isolation and purification of the desired product from this reaction mixture is needed. And it is usually difficult.

On the other hand, available processes for preparing α-bromo(methylsulfonyl)acetophenone are only those wherein as shown above in (2) and (3), oxidation is first performed to give a sulfone, followed by bromination. These processes also provide a mixture of the desired α-bromo(methylsulfonyl)acetophenone, unreacted methylsulfonylacetophenone and, as a by-product, α-dibromo(methylsulfonyl)acetophenone. Consequently, the processes are not suitable for industrial manufacture of the compound because of difficulty in isolation and purification and unsatisfactory values of yields.

SUMMARY OF THE INVENTION

An object of the present invention is to provide a process for preparing α-halo(methylthio)acetophenone in an industrially simple and economically advantageous manner.

Another object of the invention is to provide a process for preparing α-halo(methylsulfonyl)acetophenone in an industrially simple and economically advantageous manner.

The inventors of the present invention conducted extensive research to achieve the foregoing objects and found that when methylthioacetophenone used as the starting material is halogenated in the presence of an alcohol, α-halo(methylthio)acetophenone can be selectively produced in a high yield, and that when the obtained α-halo(methylthio)acetophenone is subsequently oxidized, α-halo(methylsulfonyl)acetophenone can be selectively produced in a high yield.

The first invention is directed to a process for preparing α-halo(methylthio)acetophenone represented by the formula (2), the process comprising the step of halogenating methylthioacetophenone represented by the formula (1) with a halogenating agent in the presence of an alcohol:

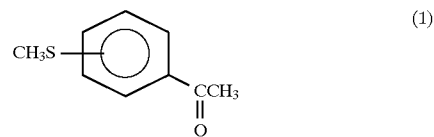

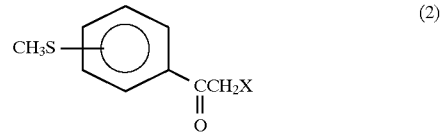

wherein X is a chlorine atom or a bromine atom.

The second invention is directed to a process for preparing α-halo(methylsulfonyl)acetophenone represented by the formula (3), the process comprising the steps of halogenating methylthioacetophenone represented by the formula (1) with a halogenating agent in the presence of an alcohol to give α-halo(methylthio)acetophenone represented by the formula (2), and oxidizing the α-halo(methylthio)acetophenone of the formula (2) with an oxidizing agent:

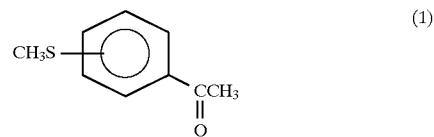

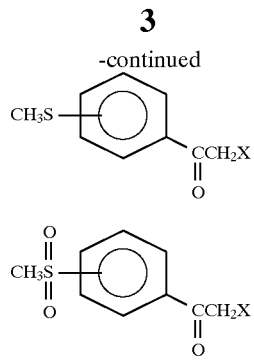

wherein X is a chlorine atom or a bromine atom.

The methylthioacetophenone of the formula (1) prepared by any conventional processes can be used as the starting material in the present invention, and it is easily prepared according to the process for preparing alkylphenylsulfone which was proposed by the present inventors (Japanese Patent Application No.289766/1994).

According to the proposed process, methylthio-acetophenone can be easily prepared by reacting halo-acetophenone with methyl mercaptan in the presence of a base and a quaternary ammonium salt catalyst in water or a mixture of water and a water-insoluble organic solvent in a heterogeneous system.

The α-halo(methylthio)acetophenone of the formula (2) can be prepared by halogenating methylthioacetophenone of the formula (1).

The α-halo(methylthio)acetophenone of the formula (2) can be prepared in a high yield if the halogenation is effected in the presence of an alcohol. Examples of alcohols which can be used are methanol, ethanol, n-propanol, isopropanol, n-butanol, sec-butanol and the like. Among them, methanol is preferred from the economical viewpoint. The amount of the alcohol to be used is not specifically limited, but usually from 0.1 to 20 times, preferably 1 to 10 times, the weight of the methylthioacetophenone of the formula (1).

Examples of useful halogenating agents are bromine, chlorine, sulfuryl bromide, sulfuryl chloride, N-bromosuccinimide and dibromodicyanomethane. Among them, bromine and chlorine are preferred because of ease of handling and from the economical viewpoint.

The amount of the halogenating agent to be used is usually 0.8 to 2 moles, preferably 1 to 1.2 moles, per mole of the methylthioacetophenone of the formula (1).

Solvents to be used are not specifically limited in the present invention. The alcohol employed in the reaction may be used as the solvent. Useful solvents include, for example, hydrocarbons such as hexane, cyclohexane and heptane; halogenated hydrocarbons such as dichloroethane, dichloromethane and chloroform; aromatic hydrocarbons such as benzene, toluene, xylene, chlorobenzene, dichlorobenzene and trichlorobenzene; and mixtures thereof. The amount of the solvent to be used is not critical but usually from 0.1 to 10 times the weight of the methylthioacetophenone of the formula (1).

The reaction temperature in the halogenation is usually about −20° to about 120° C., preferably about 0 to about 50° C. If the reaction temperature is lower, a low reaction rate would result, whereas a higher reaction temperature would cause a side reaction which would induce the reduction of a yield. Hence the reaction temperature outside said range is undesirable. The reaction time is usually 0.5 to 20 hours.

The α-halo(methylthio)acetophenone of the formula (2) thus produced can be isolated from the reaction mixture by conventional separation methods such as distillation, crystallization or the like.

Specific examples of the α-halo(methylthio) acetophenone of the formula (2) thus produced include α-bromo(2-methylthio)acetophenone, α-bromo(3-methylthio)acetophenone, α-bromo(4-methylthio) acetophenone, α-chloro(2-methylthio)acetophenone, α-chloro(3-methylthio)acetophenone and α-chloro(4-methylthio)acetophenone.

The desired α-halo(methylsulfonyl)acetophenone of the formula (3) can be prepared by subsequent oxidation of the obtained α-halo(methylthio)acetophenone of the formula (2).

The reaction mixture obtained by halogenation can be used without isolation of the α-halo(methylthio) acetophenone of the formula (2) in the preparation of the α-halo(methylsulfonyl)acetophenone of the formula (3).

The oxidation of the α-halo(methylthio)acetophenone proceeds by the addition of an oxidizing agent. Examples of useful oxidizing agents are an aqueous solution of hydrogen peroxide, organic peracids such as peracetic acid and m-chloroperbenzoic acid, and inorganic oxidizing agents such as permanganate, chromate and peroxosulfuric acid. Among them, an aqueous solution of hydrogen peroxide is preferred in view of safety, environmental problem and economy.

The amount of the oxidizing agent to be used is variable and indeterminable according to the type of the oxidizing agent used but usually from 1.5 to 10 mole equivalents, preferably 2 to 4 mole equivalents, per mole equivalent of the α-halo(methylthio)acetophenone of the formula (2).

If oxidation using an aqueous solution of hydrogen peroxide as an oxidizing agent is carried out in the presence of a catalyst, for example, sodium tungstate or the like, the reaction would smoothly proceed. The amount of the catalyst to be used would suffice if it is 0.001 to 0.1 times the weight of the α-halo(methylthio)acetophenone of the formula (2).

If oxidation using an aqueous solution of hydrogen peroxide is conducted in the presence of an acid, the reaction would proceed more smoothly. Examples of useful acids are mineral acids such as hydrochloric acid, sulfuric acid, nitric acid and phosphoric acid; and organic acids such as acetic acid and benzoic acid. Among them, hydrochloric acid, sulfuric acid and acetic acid are preferred. The amount of the acid to be used would suffice if it is 0.01 to 1 times the weight of the α-halo(methylthio)acetophenone of the formula (2).

Solvents to be used in the oxidation are not specifically limited and include, for example, water; hydrocarbons such as hexane, cyclohexane and heptane; halogenated hydrocarbons such as dichloroethane, dichloromethane and chloroform; aromatic hydrocarbons such as benzene, toluene, xylene, chlorobenzene, dichlorobenzene and trichlorobenzene; alcohols such as methanol, ethanol, n-propanol, isopropanol, n-butanol and sec-butanol; and ketones such as acetone, methyl ethyl ketone and methyl isobutyl ketone; and mixtures thereof. The amount of the solvent to be used is not critical but usually from 0.1 to 10 times the weight of the α-halo(methylthio)acetophenone of the formula (2).

The reaction temperature is usually about 0° to about 100° C., preferably about 20° to about 70° C. If the reaction temperature is lower, a low reaction rate would result, whereas a higher reaction temperature would cause a side reaction which would induce the reduction of a yield. Hence the reaction temperature outside said range is undesirable. The reaction time is about 1 to about 10 hours.

In this way, the desired α-halo(methylsulfonyl)-acetophenone of the formula (3) can be produced. The α-halo(methylsulfonyl)acetophenone thus produced can be isolated from the reaction mixture by conventional separation methods such as extraction, crystallization or distillation.

Specific examples of the α-halo(methylsulfonyl)-acetophenone of the formula (3) thus produced include α-bromo(2-methylsulfonyl)acetophenone, α-bromo(3-methylsulfonyl)acetophenone, α-bromo(4-methyl-sulfonyl) acetophenone, α-chloro(2-methylsulfonyl)acetophenone, α-chloro(3-methylsulfonyl)acetophenone and α-chloro(4-methylsulfonyl)acetophenone.

The present invention provides novel processes for preparing α-halo(methylthio)acetophenone and α-halo(methylsulfonyl)acetophenone which are useful, for example, as an intermediate for preparing pharmaceuticals. According to each process of the present invention, the desired compound can be selectively produced in a high yield by a simple and safe procedure of halogenation of methylthioacetophenone or its halogenation followed by oxidation. Consequently the processes of the invention are of high economical and industrial values.

DETAILED DESCRIPTION OF BEST MODE FOR CARRYING OUT THE INVENTION

The present invention is described below in greater detail with reference to the following Examples to which, however, the invention is not limited at all.

EXAMPLE 1

Into a 2-liter four-necked flask equipped with a stirrer, thermometer, dropping funnel and reflux condenser were placed 166 g (1.00 mole) of 4-methylthioacetophenone and 500 g of methanol. To the mixture was added dropwise 160 g (1.00 mole) of bromine at 20° to 30° C. over a period of 1 hour, followed by stirring for 10 minutes. After addition of 600 g of water, 240 g of α-bromo(4-methylthio) acetophenone was produced by crystallization. The yield of the obtained compound based on 4-methylthioacetophenone was 98.0%.

EXAMPLE 2

Into a 2-liter four-necked flask equipped with a stirrer, thermometer, dropping funnel and reflux condenser were placed 166 g (1.00 mole) of 4-methylthioacetophenone and 420 g of methanol. To the mixture was added dropwise 160 g (1.00 mole) of bromine at 20° to 30° C. over a period of 1.5 hours, followed by stirring for 10 minutes. Thereafter 780 g of methanol, 0.4 g of sodium tungstate and 100 g of acetic acid were added. Then, 283 g (2.50 moles) of a 30% aqueous solution of hydrogen peroxide was added dropwise over a period of 1.5 hours with stirring at 50° C. The reaction mixture was stirred for 5 hours to complete the reaction. The reaction mixture was cooled to 5° C. and 240 g of α-bromo(4-methylsulfonyl)acetophenone was produced by crystallization. The yield of the obtained compound based on 4-methylthioacetophenone was 86.5%.

EXAMPLE 3

The same procedure as in Example 2 was repeated with the exception of using 166 g (1.00 mole) of 2-methylthioacetophenone in place of 4-methylthioacetophenone, producing 230 g of α-bromo(2-methylsulfonyl)acetophenone. The yield of the obtained compound based on 2-methylthioacetophenone was 83.2%.

EXAMPLE 4

Into a 2-liter four-necked flask equipped with a stirrer, thermometer, dropping funnel and reflux condenser were placed 166 g (1.00 mole) of 4-methylthioacetophenone and 500 g of methanol. To the mixture was added dropwise 160 g (1.00 mole) of bromine at 20° to 30° C. over a period of 1 hour, followed by stirring for 10 minutes. After addition of 600 g of water, 240 g (0.98 mole) of α-bromo(4-methylthio) acetophenone was produced by crystallization. Thereafter 600 g of acetone, 2.0 g of sodium tungstate and 5.0 g of concentrated sulfuric acid were added to the obtained crystals. To the mixture was added dropwise 283 g (2.50 moles) of a 30% aqueous solution of hydrogen peroxide over a period of 1 hour with stirring at 50° C. The reaction mixture was stirred for 1 hour to complete the reaction. After addition of 600 g of water, 253 g of α-bromo(4-methylsulfonyl)acetophenone was produced by crystallization. The yield of the obtained compound based on 4-methylthioacetophenone was 91.3%.

EXAMPLE 5

Into a 2-liter four-necked flask equipped with a stirrer, thermometer, gas inlet and reflux condenser were placed 166 g (1.00 mole) of 4-methylthioacetophenone and 500 g of methanol. Then, 71.0 g (1.00 mole) of chlorine was blown at 20° to 30° C. over a period of 2 hours, followed by stirring for 10 minutes. After addition of 600 g of water, 156 g (0.78 mole) of α-chloro(4-methylthio)acetophenone was produced by crystallization. Thereafter 600 g of acetone, 2.0 g of sodium tungstate and 5.0 g of concentrated sulfuric acid were added to the obtained crystals. To the mixture was added dropwise 283 g (2.50 moles) of a 30% aqueous solution of hydrogen peroxide over a period of 1 hour with stirring at 50° C. The reaction mixture was further stirred for 1 hour to complete the reaction. After addition of 600 g of water, 176 g of α-chloro(4-methylsulfonyl)acetophenone was produced by crystallization. The yield of the obtained compound based on 4-methylthioacetophenone was 75.7%.

We claim:

1. A process for preparing α-halo(methylthio)-acetophenone represented by the formula (2), the process comprising the step of halogenating methylthioacetophenone represented by the formula (1) with a halogenating agent in the presence of an alcohol:

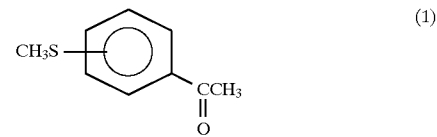

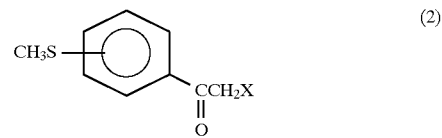

wherein X is a chlorine atom or a bromine atom.

2. The process according to claimn 1, wherein the halogenating agent is chlorine or bromine.

3. The process according to claim 1, wherein the alcohol is methanol.

4. A process for preparing α-halo(methyl-sulfonyl) acetophenone represented by the formula (3), the process comprising the steps of halogenating methylthioacetophenone represented by the formula (1) with a halogenating agent in the presence of an alcohol to give α-halo (methylthio)acetophenone represented by the formula (2), and oxidizing the α-halo(methylthio)acetophenone of he formula (2) with an oxidizing agent:

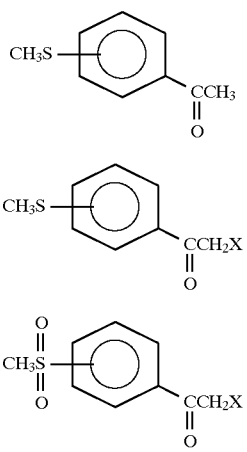

wherein X is a chlorine atom or a bromine atom.

5. The process according to claim 4, wherein the halogenating agent is chlorine or bromine.

6. The process according to claim 4, wherein the alcohol is methanol.

7. The process according to claim 4, wherein the oxidizing agent is an aqueous solution of hydrogen peroxide.

8. The process according to claim 7, wherein the oxidation is effected in the presence of a sodium tungstate catalyst.

9. The process according to claim 7, wherein the oxidation is carried out in the presence of an acid.

10. The process according to claim 1, wherein the alcohol is used in an amount 0.1–20 times that of the methylthioacetophenone by weight.

11. The process according to claim 10, wherein the alcohol is used in an amount 1–10 times that of the methylthioacetophenone by weight.

12. The process according to claim 10, wherein the alcohol is selected from the group consisting of methanol, ethanol, n-propanol, isopropanol, n-butanol, and sec-butanol.

13. The process according to claim 4, wherein the alcohol is used in an amount 0.1–20 times that of the methylthioacetophenone by weight.

14. The process according to claim 13, wherein the alcohol is used in an amount 1–10 times that of the methylthioacetophenone by weight.

15. The process according to claim 13, wherein the alcohol is selected from the group consisting of methanol, ethanol, n-propanol, isopropanol, n-butanol, and sec-butanol.

* * * * *

UNITED STATES PATENT AND TRADEMARK OFFICE
CERTIFICATE OF CORRECTION

PATENT NO. : 5,821,388
DATED : October 13, 1998
INVENTOR(S) : Junichi Sakamoto, Hideaki Nishiguchi and Hiroshi Goda It is certified that error appears in the above-identified patent and that said Letters Patent is hereby corrected as shown below:

On the title page: Item [73] Assignee, please correct "Sumitomo Seika Chemical Co., Ltd." to --Sumitomo Seika Chemicals Co., Ltd.--

Signed and Sealed this

Twenty-third Day of February, 1999

Attest:

Q. TODD DICKINSON

Attesting Officer

Acting Commissioner of Patents and Trademarks